United States Patent
Sasady et al.

(10) Patent No.: US 11,647,981 B2
(45) Date of Patent: May 16, 2023

(54) ULTRASOUND IMAGING PROBE

(71) Applicant: B-K Medical Aps, Herlev (DK)

(72) Inventors: Niels-Christian Sasady, Frederiksberg (DK); Per Ehrenreich Nygaard, Soeborg (DK); Bo Hansen, Vanlose (DK)

(73) Assignee: B-K MEDICAL APS, Herlev (DK)

( * ) Notice: Subject to any disclaimer, the term of this patent is extended or adjusted under 35 U.S.C. 154(b) by 811 days.

(21) Appl. No.: 15/307,420

(22) PCT Filed: Apr. 29, 2014

(86) PCT No.: PCT/IB2014/061083
§ 371 (c)(1),
(2) Date: Oct. 28, 2016

(87) PCT Pub. No.: WO2015/166302
PCT Pub. Date: Nov. 5, 2015

(65) Prior Publication Data
US 2017/0065250 A1    Mar. 9, 2017

(51) Int. Cl.
*A61B 8/12* (2006.01)
*A61B 1/008* (2006.01)
(Continued)

(52) U.S. Cl.
CPC ............ *A61B 8/12* (2013.01); *A61B 1/008* (2013.01); *A61B 1/00174* (2013.01);
(Continued)

(58) Field of Classification Search
CPC ........... A61B 1/01; A61B 1/3132; A61B 8/12; A61B 8/0841; A61B 1/00174;
(Continued)

(56) References Cited

U.S. PATENT DOCUMENTS

| 4,763,662 A | 8/1988 | Yokoi | |
|---|---|---|---|
| 5,658,306 A * | 8/1997 | Kieturakis | A61B 17/3403 128/898 |

(Continued)

FOREIGN PATENT DOCUMENTS

| EP | 0668052 A2 | 8/1995 |
|---|---|---|
| EP | 2138092 A1 | 12/2009 |
| WO | 2013008047 A1 | 1/2013 |

OTHER PUBLICATIONS

International Search Report for PCT/IB2014/061083 published as WO2015/166302 A1 dated Nov. 5, 2015.

*Primary Examiner* — Chao Sheng

(74) *Attorney, Agent, or Firm* — Daugherty & Del Zoppo, Co. LPA

(57) ABSTRACT

An ultrasound probe (104) includes a probe head (134). The probe head includes a transducer array (136) with a transducing surface (137), an instrument guide (142), and a light source (140). A method includes emitting a light beam, from a light source disposed on and adjacent to a transducer array of an ultrasound imaging probe, in a direction opposite of a transducing surface of the transducer array, at an inside wall of a cavity of a subject or object. A laparoscopic ultrasound imaging probe includes a shaft, a body, an articulating member that couples the probe head, and a handle coupled to the elongate shaft. The articulating probe head includes a transducer array that generates an ultrasound signal that traverses an image plane of the transducer array, an instrument guide, and a light source arranged to emit light in a direction opposite of the image plane.

16 Claims, 8 Drawing Sheets

(51) Int. Cl.
*A61B 1/313* (2006.01)
*A61B 8/00* (2006.01)
*A61B 1/00* (2006.01)
*A61B 8/08* (2006.01)
*A61B 8/14* (2006.01)

(52) U.S. Cl.
CPC ............ *A61B 1/3132* (2013.01); *A61B 8/085* (2013.01); *A61B 8/0833* (2013.01); *A61B 8/14* (2013.01); *A61B 8/4466* (2013.01); *A61B 8/4483* (2013.01); *A61B 8/461* (2013.01); *A61B 8/5215* (2013.01); *A61B 8/0841* (2013.01); *A61B 8/4488* (2013.01)

(58) Field of Classification Search
CPC ....... A61B 1/008; A61B 8/0833; A61B 8/085; A61B 8/14; A61B 8/4466; A61B 8/4483; A61B 8/461; A61B 8/5215; A61B 8/4488
See application file for complete search history.

(56) References Cited

U.S. PATENT DOCUMENTS

| | | | |
|---|---|---|---|
| 6,083,169 A | 7/2000 | Hansen | |
| 6,149,598 A * | 11/2000 | Tanaka | A61B 8/12 600/437 |
| 6,409,666 B1 | 6/2002 | Ito | |
| 2004/0143252 A1* | 7/2004 | Hurst | A61B 18/1477 606/41 |
| 2005/0228289 A1* | 10/2005 | Kohno | A61B 1/018 600/463 |
| 2006/0036164 A1* | 2/2006 | Wilson | A61B 5/06 600/424 |
| 2007/0239010 A1* | 10/2007 | Johnson | A61B 8/12 600/439 |
| 2007/0270653 A1* | 11/2007 | Vayser | A61B 1/00135 600/182 |
| 2008/0161696 A1 | 7/2008 | Schmitt et al. | |
| 2008/0183043 A1* | 7/2008 | Spinnler | A61B 1/0676 348/E5.029 |
| 2008/0194945 A1* | 8/2008 | Kukuk | A61B 5/055 600/424 |
| 2008/0242975 A1* | 10/2008 | Tsui | A61B 8/0841 600/424 |
| 2008/0287961 A1* | 11/2008 | Miyamoto | A61B 1/00098 606/127 |
| 2009/0171218 A1 | 7/2009 | Nygaard et al. | |
| 2013/0012811 A1* | 1/2013 | Schmitt | A61B 5/0066 600/427 |
| 2013/0184680 A1* | 7/2013 | Brewer | A61M 25/0612 604/510 |
| 2015/0223677 A1* | 8/2015 | Schouwink | A61B 1/0623 600/178 |

* cited by examiner ated probe includes a transducer
ULTRASOUND IMAGING PROBE

RELATED APPLICATION

This application is a national filing of PCT application Ser. No. PCT/IB2014/061083, filed Apr. 29, 2014, published as WO2015/166302 on Nov. 5, 2015. This application claims priority to PCT application Ser. No. PCT/IB2014/061083, published as WO2015/166302 on Nov. 5, 2015.

TECHNICAL FIELD

The following generally relates to ultrasound and more particularly to an ultrasound probe and is described with particular application to ultrasound imaging.

BACKGROUND

An ultrasound imaging system has included an ultrasound probe with a transducer array and a console. The ultrasound probe houses a transducer array, and the console includes a display monitor and a user interface. The transducer array transmits an ultrasound signal into a field of view and receives echoes produced in response to the signal interacting with structure therein. The echoes are processed, producing images of the scanned structure, which may be visually presented through the display monitor. An example ultrasound probe is a laparoscopic ultrasound probe. A laparoscopic ultrasound probe has been used to guide a needle to structure of interest inside of a cavity of an object or subject, e.g., in connection with a biopsy, radio frequency (RF) ablation, etc.

One approach includes using a needle that is wound around the ultrasound probe and supported adjacent to the transducer array. The transducer array and hence the needle are guided to the structure of interest through ultrasound or other images. In another approach, the needle is first attached to the transducer array outside of the cavity. Then, the other end of the needle is fed through a trocar into the cavity. Forceps are inserted into the cavity through another trocar and used to grasp the needle in the cavity and pull it up through the trocar. Concurrently, the ultrasound probe is fed into the cavity through the first trocar. The transducer array and hence the needle can then be guided to the structure.

Examples of the above two approaches are described in U.S. Pat. No. 6,086,169, filed Apr. 19, 1996, and entitled "Method and an apparatus for the insertion of a needle guide into a patient in order to remove tissue samples," which is incorporated by reference in its entirety herein. Unfortunately, the above approaches utilize a long flexible needle that can be expensive (e.g., relative to a free hand needle) and difficult to use. Furthermore, the second approach requires predicting where to insert the needle through the cavity wall to reach the structure of interest, which may require a high degree of skill, and may result in a less than optimal site for the guiding the needle to the structure of interest.

SUMMARY

Aspects of the application address the above matters, and others.

In one aspect, an ultrasound probe includes a probe head. The probe head includes a transducer array with a transducing surface, an instrument guide, and a light source.

In another aspect, a method includes emitting a light beam, from a light source disposed on and adjacent to a transducer array of an ultrasound imaging probe, in a direction opposite of a transducing surface of the transducer array, at an inside wall of a cavity of a subject or object.

In another aspect, a laparoscopic ultrasound imaging probe includes a shaft, a body, an articulating member that couples the probe head, and a handle coupled to the elongate shaft. The articulating probe head includes a transducer array that generates an ultrasound signal that traverses an image plane of the transducer array, an instrument guide, and a light source arranged to emit light in a direction opposite of the image plane.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
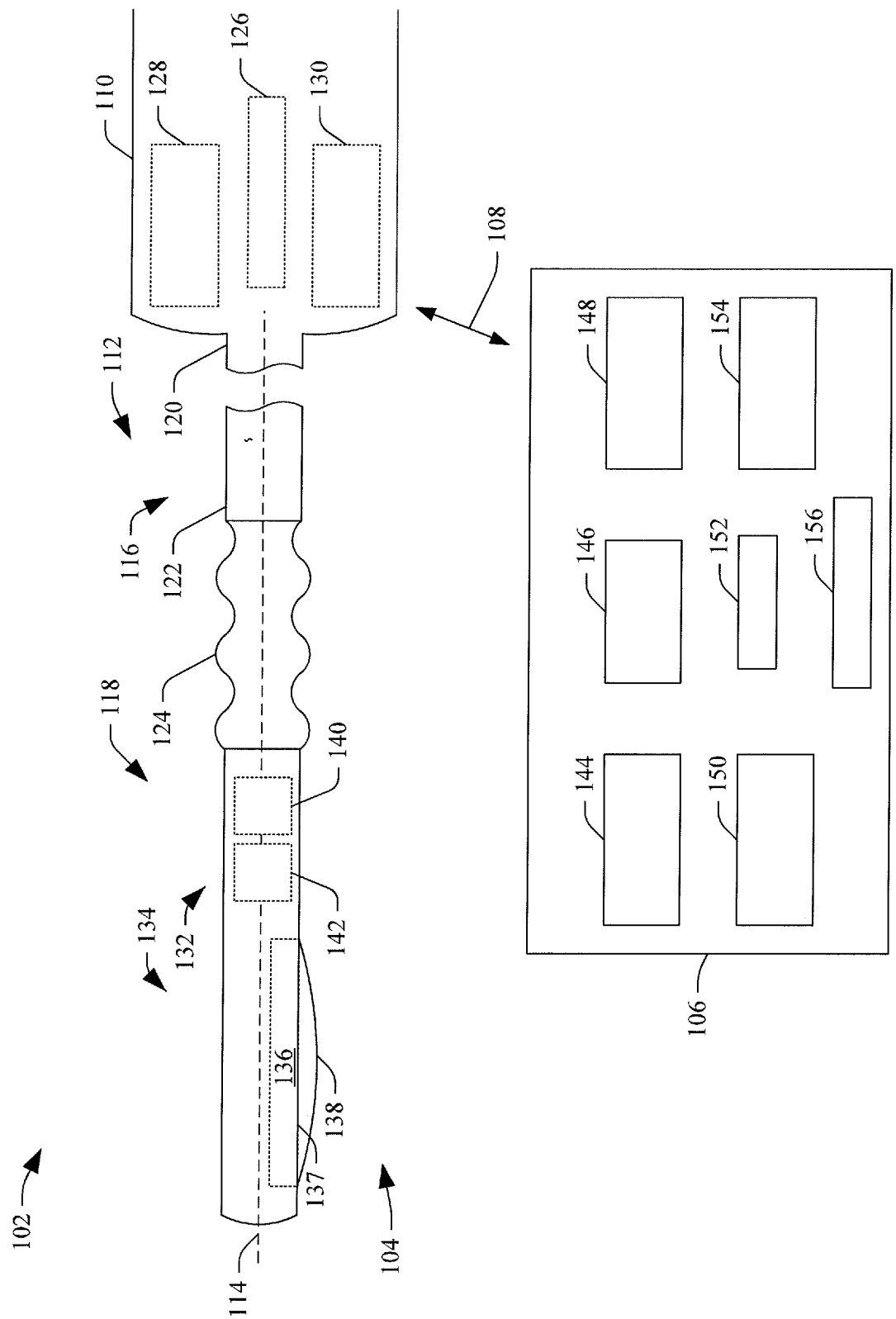
FIG. 1 schematically illustrates an example probe with a light source and an instrument guide.

FIG. 1 schematically illustrates an imaging system 102 such as ultrasound imaging system. The imaging system 102 includes an ultrasound probe 104 and a console 106. The ultrasound probe 104 and the console 106 are in electrical communication through a communications channel 108, which may be through a wireless or a hard wire (e.g., electro-mechanical connector, a cable, etc.) communications channel.

The ultrasound probe 104 includes a handle 110 and an elongate shaft 112 having a long axis 114. The elongate shaft 112 includes a body 116 and a head 118, both aligned along the long axis 114. The body 116 includes a first end 120 and a second opposing end 122. The first end 120 of the body is affixed to the handle 110. An articulating member 124 couples the second end 122 of the body and the head 118. The articulating member 124 articulates in at least four directions. In a variation, the articulating member 124 is omitted and the ultrasound probe 104 is a rigid, or non-articulating, probe.

Figure 2:
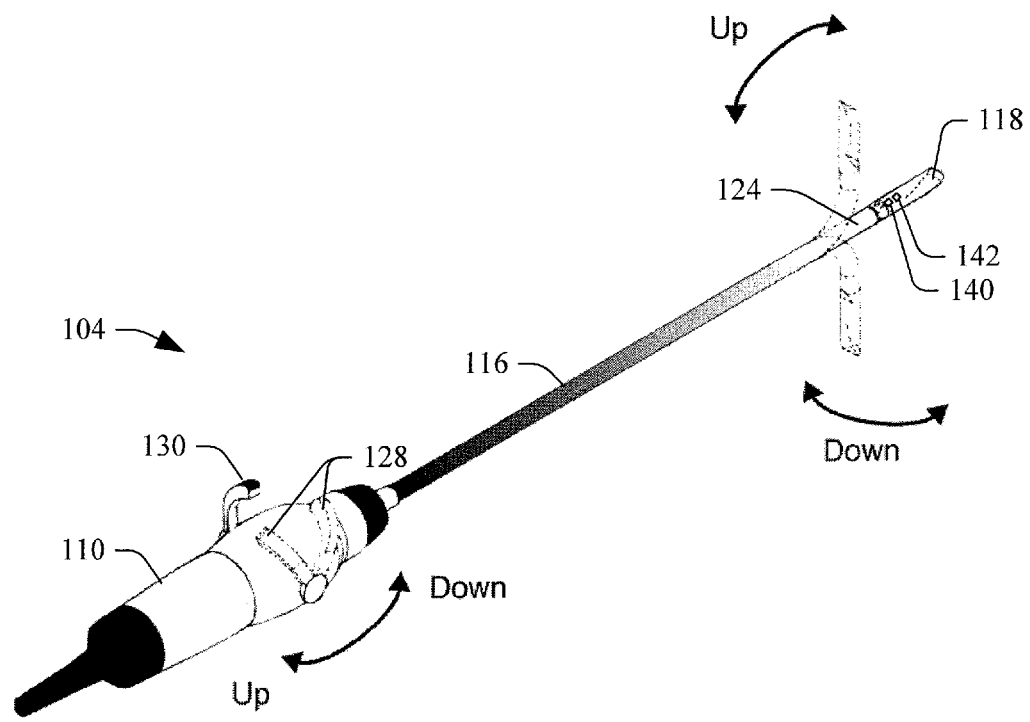
FIG. 2 illustrates example up/down movement of a head of the probe.
Figure 3:
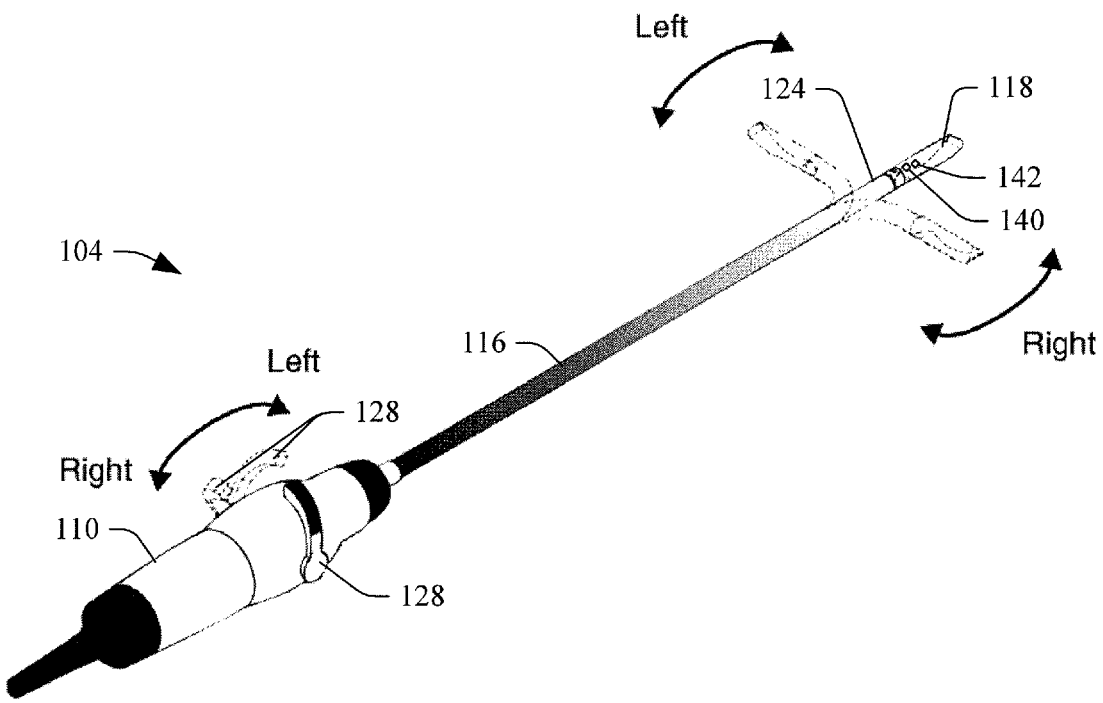
FIG. 3 illustrates example right/left movement of the head of the probe.

The handle 110 includes electronics 126, a first actuator 128 and a second actuator 130. The electronics 126 provide power and/or data channels. The first actuator 128 actuates the articulating member 124 to control up/down movement of the head 118. The second actuator 130 actuates the articulating member 124 to control left/right movement of the head 118. FIGS. 2 and 3 respectively show example actuation of the actuators 128 and 130 and corresponding up/down and left/right movement of the head 118.

An example of a transducer probe with an articulating head is the transducer data type 8666, which is a product of BK-Medical ApS, a company of Herlev, Denmark, which is a wholly owned subsidiary of Analogic Corporation, a company of MA, USA. Example approaches for articulating an articulating head of a transducer probe with an articulating head are described in patent applications PCT/IB2011/001622 and PCT/IB2013/000043, which are incorporated herein by reference in their entireties.

The head 118 includes a first end region 132 and a second opposing end region 134. A transducer array 136 is disposed in the second end region 134. The transducer array 136 includes a one-dimensional (1D) or two-dimensional (2D) array of transducer elements. Suitable arrays include linear, curved (e.g., convex), phased, etc. The transducer array 136 can be fully populated or spares. The transducer array 136 includes a transducing surface 137. An ultrasonic window 138 is disposed adjacent to a transducing side of transducer array 136.

A light source 140 and an instrument guide 142 are disposed in the first end region 132. As described in greater detail below, the light source 140 is arranged with respect to the instrument guide 142 to illuminate, when inside a cavity, a region on an inside wall of cavity, which aligns with a path traversing the slot of the instrument guide 142. As such, a clinician, e.g., guided by a laparoscopic camera, can identify an instrument insertion point on an outside wall of the cavity. For example, the clinician can press around on the outside of the cavity until the depression on the inside wall of the cavity aligns with the illuminated region. This assures the clinician that the insertion point will allow a free hand instrument to reach the instrument guide 142, e.g., under ultrasound image guidance, for guidance of the instrument to a structure of interest inside of the cavity.

The probe 104 can be used for laparoscopic, endoscopic, and/or other ultrasound applications, and can be used to assist personnel, for example, with an interventional procedure such as a liver, gall bladder, tumor biopsy, etc., guide personnel, for example, with biopsy, RF ablation, chemical injection, etc. As shown, the probe 104 is employed with the console 106. In other embodiments, the probe 104 can be employed with other consoles and/or devices, via cable or wireless communication.

The console 106 includes a transmit circuit 144 and a receive circuit 146. The transmit circuit 144 controls the phasing and/or time of actuation of the individual elements of the transducer array 136, which allows for steering and/or focusing the transmitted beam. The receive circuit 146 receives signals indicative of the echoes received by the transducer array 136 and can beamform (e.g., delay and sum) the received echoes.

The console 106 further includes an echo processor 148 that processes received echoes. Such processing may include beamforming (e.g., delay and sum) the echoes. For example, with B-mode, the echo processor 148 can produce a sequence of focused, coherent echo samples along focused scanlines of a scanplane. Other processing may lower speckle, improve specular reflector delineation, and/or includes FIR filtering, IIR filtering, etc.

The console 106 further includes a scan converter 150 that scan converts (using analog and/or digital scan converting techniques) the frames of data to generate data for display, for example, by converting the data to the coordinate system of the display. This may include changing the vertical and/or horizontal scan frequency of signal based on the display. The console 106 further includes a display 152 that visually presents the scan converted data.

The console 106 further includes a user interface (UI) 154 with one or more input devices (e.g., a button, a knob, a touchscreen, etc.) and/or one or more output devices (e.g., a display monitor, an audio presenter, etc.), which allows for interaction with the system 102. The console 106 further includes a controller 156 that controls at least one of the transmit circuit 144, the receive circuit 146, the echo processor 148, the scan converter 150, the display 152 or the user interface 154.

At least one of the components of the console 106 can be implemented by way of computer readable instructions, encoded or embedded on computer readable storage medium (which excludes transitory medium) including physical memory and/or other non-transitory medium, which, when executed by a computer processor(s), causes the processor (s) to carry out functions. At least one of the instructions, optionally, is carried by a signal, carrier wave or other transitory medium.

Figure 4:
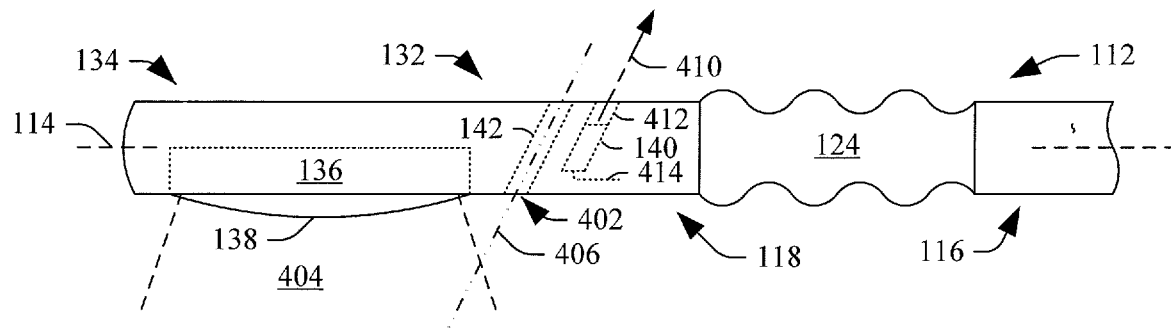
FIG. 4 schematically illustrates a side view of the head of the probe.
Figure 5:
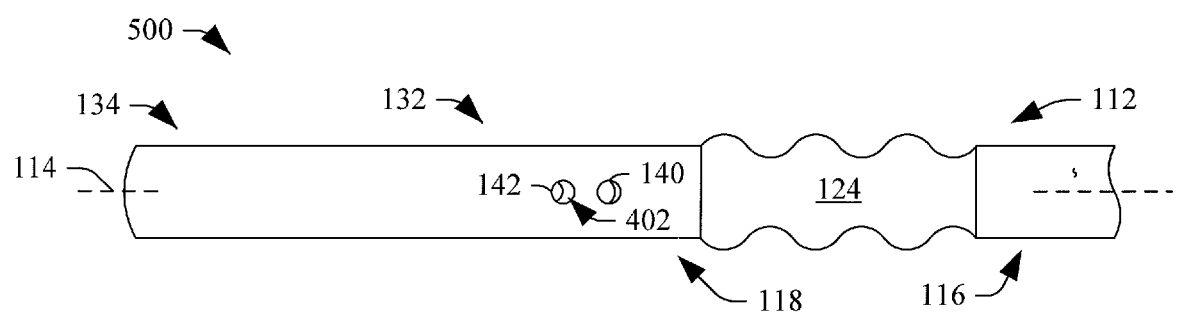
FIG. 5 schematically illustrates a top down view of the head of the probe.
Figure 6:
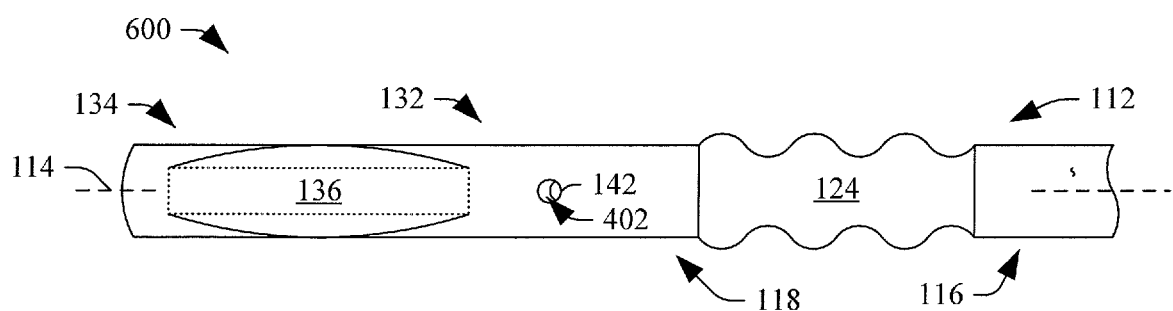
FIG. 6 schematically illustrates a bottom up view of the head of the probe.

FIGS. 4, 5 and 6 illustrate a non-limiting example of the light source 140 and the instrument guide 142. FIG. 4 shows a side view, FIG. 5 shows a top down view into a top 500, and FIG. 6 shows a bottom up view from a bottom 600.

The instrument guide 142 includes a material free region or slot 402. The slot 402 is configured to allow an instrument to pass through the instrument guide 142. For example, where the instrument is a needle, the slot 402 may have a diameter that allows a needle having a gauge in a range from 14 to 20 G (or other over or non-overlapping range) to pass. For this, the diameter may be on the order of the largest needle gauge (1.600 mm for 14 G) plus a margin (e.g., 0.050 mm or higher).

The slot 402 is angled (with respect to the long axis of the shaft 112) and extends in a direction from the transducer array 136 towards the articulating region 124. This allows a portion of an instrument advancing from the side of the handle 100 to enter the slot 402, traverse there through, and enter a field of view 404 of the transducer array 136. As an example, FIG. 4 shows an imaginary path 406 extending through the slot 402 and into the field of view 404. The angle of the illustrated slot 402 is not limiting.

The light source 140, similar to the slot 402, is angled with respect to the long axis of the shaft 112. In the illustrated embodiment, the angle of each of the light source 140 and the slot 402, with respect to the long axis of the shaft 112, is the same. The light source 140 is also off-set, along the long axis, from the slot 402. As such, the light emitted therefrom traverses a path 410, which is parallel to the path 406, in a direction from the transducer array 136 in a direction of the articulating region 124.

A window 412 provides a path for the light source 140 to exit the shaft 112. The window 412 can include a lens, a prism, a filter, and/or other optical element. With the above described configuration, a central location of the light emitted from the light source 140 will illuminate a region on the inside wall of the cavity that is off-set from the insertion point of the instrument in the cavity wall. As discussed herein, this allows the clinician to locate the insertion point for the instrument from inside the cavity.

The light source 140 can include one or more light emitting elements such as one or more of a laser, a light emitting diode (LED), an optic fiber, or the like. The light source 14 emits a light beam that generates a light spot (e.g., on an incident surface) having a diameter in a range of one (1) millimeter to fifty (50) millimeters. For example, in one instance, the light source 140 emits a light beam that generates a light spot with a diameter in a range of two (2) millimeters to four (4) millimeters.

Power for the light source 140 can be from an internal battery (re-chargeable or disposable), capacitor, etc. located in the shaft 112, the handle 110 and/or otherwise in connection with the ultrasound probe 104, and/or from an external power supply, for example, from the console 106 and/or otherwise. FIG. 4 shows an example in which power is supplied to the light source 140 through an internal electrical path 414.

Variations are described next.

Figure 7:
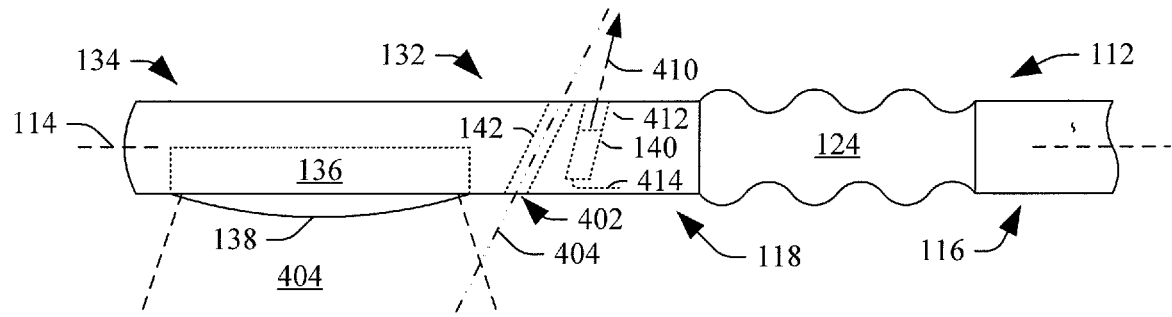
FIG. 7 schematically illustrates a variation of the light source and the instrument guide.

FIG. 7 illustrates a variation in which the light source 140 and the instrument guide 142 are at different angles. With this embodiment, the central location of the light emitted from the light source 140 will illuminate a region on the inside wall of the cavity that is closer to the insertion point and, in some instances, depending on a distance from the light source 140 and the instrument guide 142, may align with the insertion point.

Figure 8:
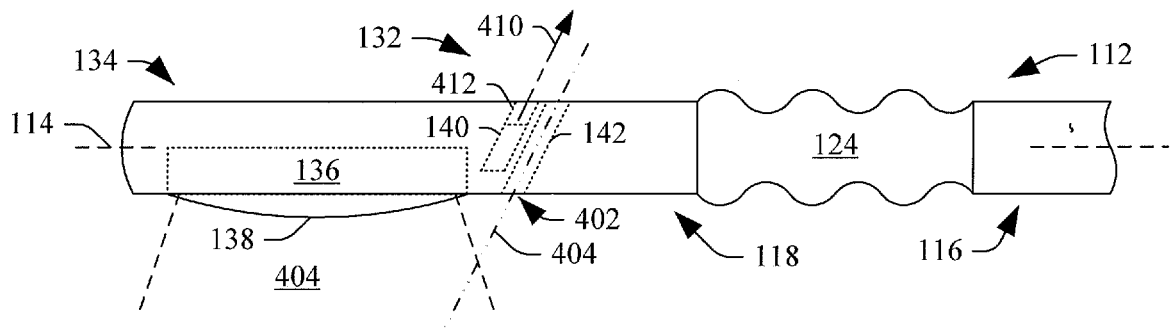
FIG. 8 schematically illustrates another variation of the light source and the instrument guide.

FIG. 8 illustrates a variation in which the location of the light source 140 and the instrument guide 142 along the long axis 114, with respect to transducer array 136, is reversed, and the light source 140 is on the transducer array 136 side and the instrument guide 142 is on the articulating member 124 side. In FIGS. 4-6, the light source 140 is on the articulating member 124 side and the instrument guide 142 is on the transducer array 136 side.

Figure 9:
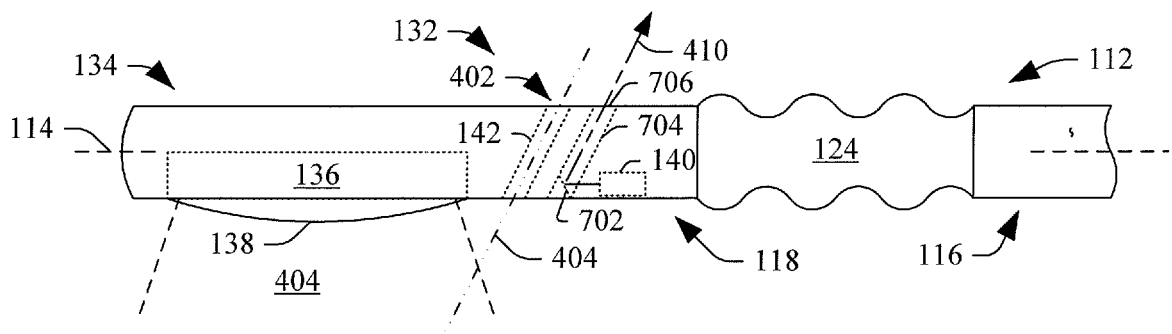
FIG. 9 schematically illustrates another variation of the light source and the instrument guide.
Figure 10:
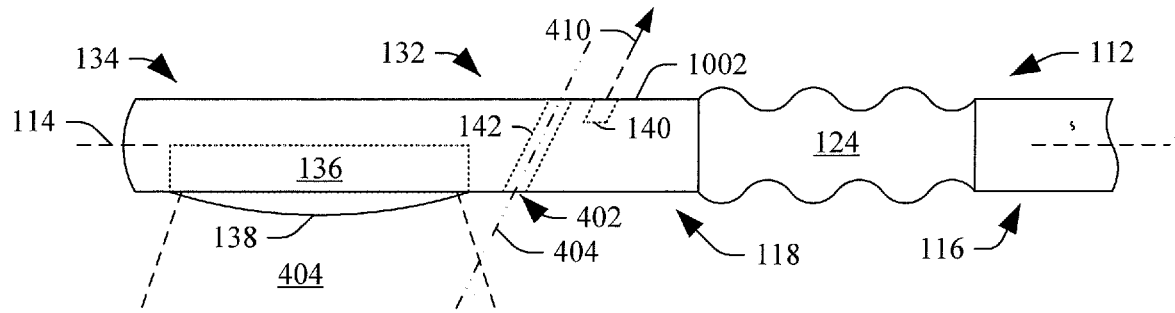
FIG. 10 schematically illustrates another variation of the light source and the instrument guide.

FIG. 9 illustrates a variation in which the light source 140 emits light in a direction of the long axis 114 and an element 702 reflects the light down a light pipe 704 and out of a window 706. The element 702 may include a mirror and/or reflective surface and/or coating. FIG. 10 illustrates a variation in which the light source 140 is flush 1002 with a surface of the shaft 112.

Figure 11:
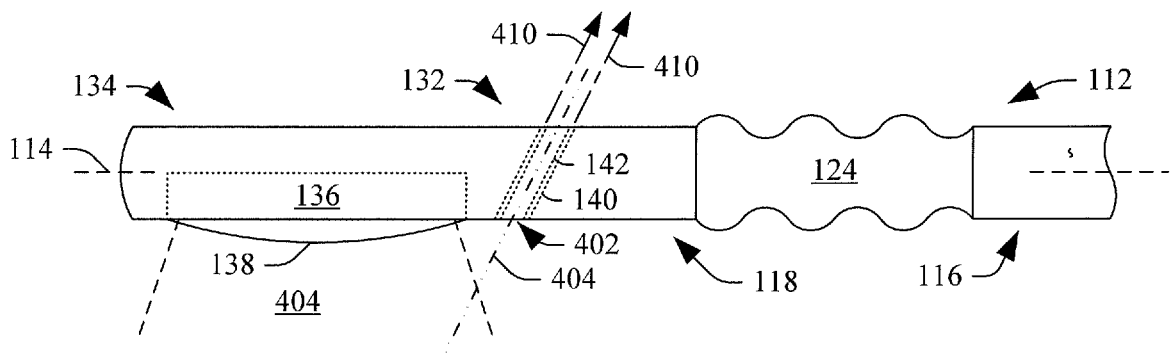
FIG. 11 schematically illustrates another variation of the light source and the instrument guide.
Figure 12:
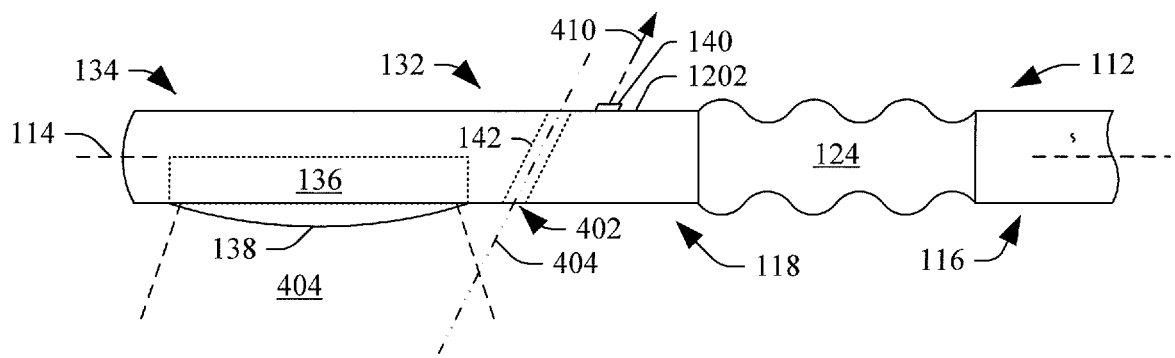
FIG. 12 schematically illustrates another variation of the light source and the instrument guide.

FIG. 11 illustrates a variation in which the light source 140 surrounds an outer perimeter of the instrument guide 142. In this variation, a central region of the light pattern on the inside wall of the cavity identifies the insertion point. FIG. 12 illustrates a variation in which the light source 140 protrudes from a surface 1202 of the shaft 112. In this variation, the window 412 is omitted.

FIG. 11 illustrates a variation in which the light source 140 surrounds an outer perimeter of the instrument guide 142. In this variation, a central region of the light pattern on the inside wall of the cavity identifies the insertion point.

FIG. 12 illustrates a variation in which the light source 140 protrudes from a surface 1202 of the shaft 112. In this variation, the window 412 is omitted.

Figure 13:
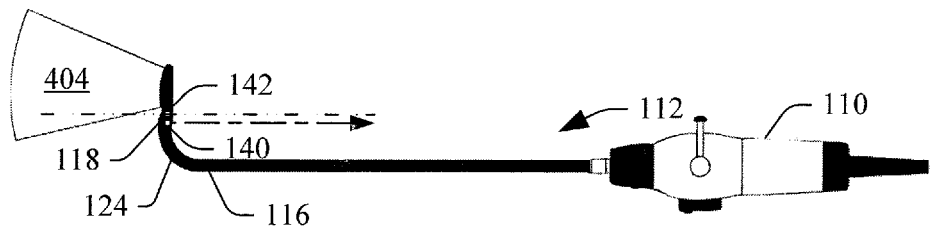
FIG. 13 schematically illustrates another variation of the light source and the instrument guide.

FIG. 13 illustrates a variation in which the light source 140 and the instrument guide 142 are not angled with respect to the head 118. In FIG. 13, the head 118 is shown in an articulated position.

Figure 14:
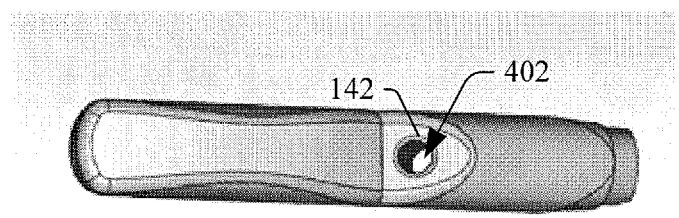
FIG. 14 schematically illustrates a variation of the instrument guide.
Figure 15:
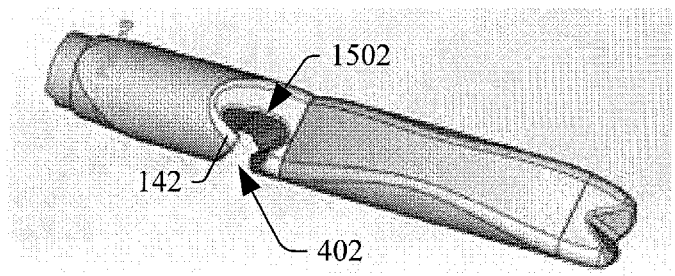
FIG. 15 schematically illustrates another variation of the instrument guide.
Figure 16:
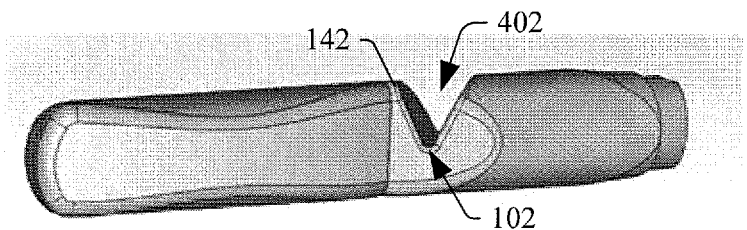
FIG. 16 schematically illustrates another variation of the instrument guide.

FIGS. 14, 15 and 16 illustrate non-limiting examples of the instrument guide 142. In FIG. 14, the slot 402 of the instrument guide 142 is cylindrical in shape. In FIG. 15, the slot 402 of the instrument guide 142 includes a "C" shape cut out 1502. In FIG. 16, the slot 402 of the instrument guide 142 includes a "V" shaped cut out 1602. Other variations are also contemplated herein. In general, the slot 402 is configured to allow an instrument of interest to pass there through.

Figure 17:
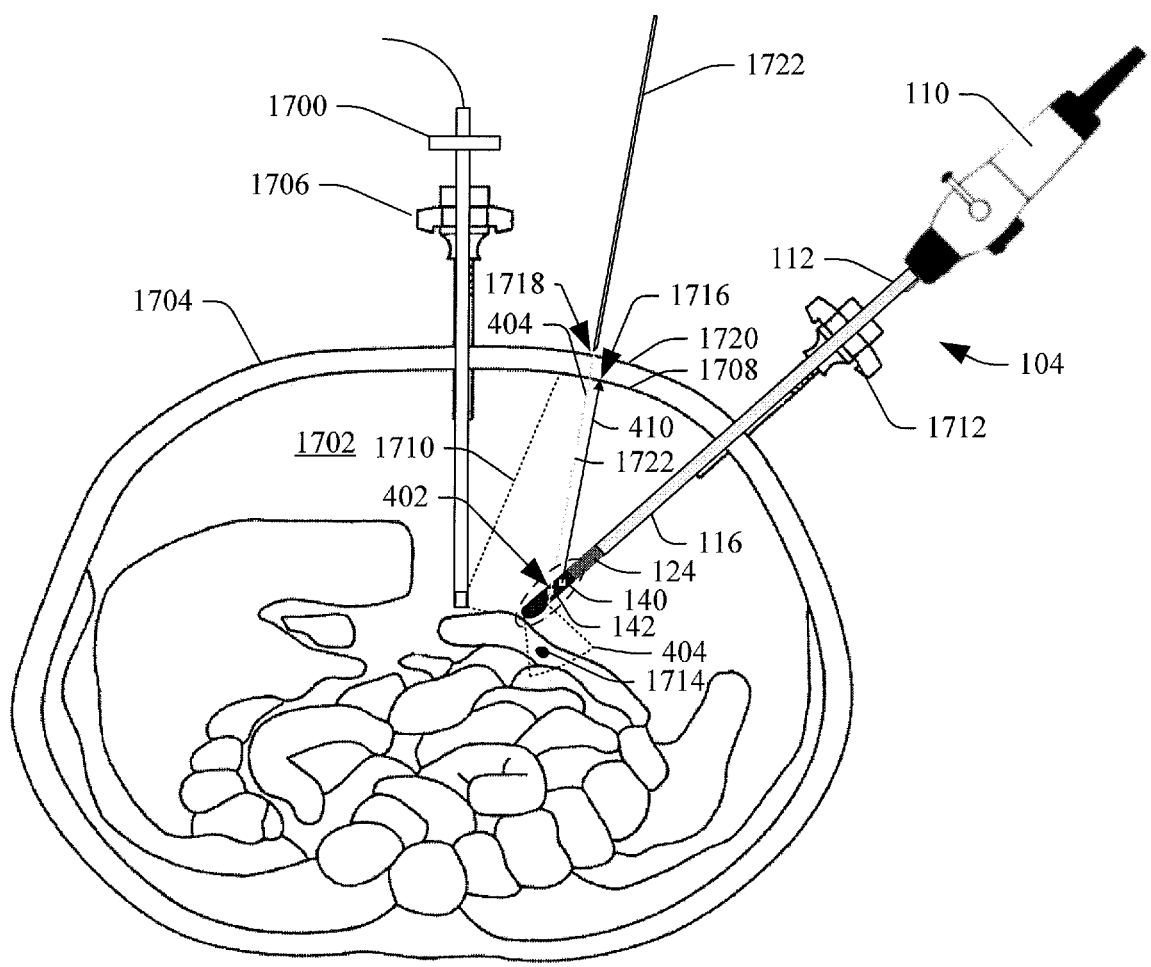
FIG. 17 illustrate the probe in operation.

FIG. 17 shows the probe 104 in use. In FIG. 17, a laparoscopic camera 1700 is inserted into an abdominal cavity 1702 of a patient 1704. The abdominal cavity 1702 is held in a distended state through a gas supplied by an insufflator or the like. The laparoscopic camera 1700 is inserted into the abdomen cavity 1702 through a first trocar 1706. The laparoscopic camera 1700 is operated so that an inside wall 1708 of the abdominal cavity 1702 is in its field of view 1710.

The head 118 of shaft 112 is also inserted into the abdominal cavity 1702 of the patient 1704. The head 118 is inserted into the abdomen cavity 1702 through a second trocar 1712. The head 118 is positioned so that a structure of interest 1714 is in the field of view 404. In this position, the light source 140 emits the light 410 which illuminates a region 1716 on the inside wall 1708 of the abdominal cavity 1702. The laparoscopic camera 1700 generates an image or video which shows the illuminated region 1716.

From the illuminated region 1716, an insertion point 1718 is located on an outside wall 1720 of the abdominal cavity 1702 by pressing on the outside wall 1720 and identifying the point at which the depression inside the wall coincides with the illuminated region 1716. A needle instrument 1722 is inserted at the insertion point 1718 and is advanced along the path 404 to the slot 402 in the instrument guide 142. The needle instrument 1722 is guided along the path 404 to the slot 402 using ultrasound and/or other image data and advanced to the structure of interest 1714 using the instrument guide 142 and the ultrasound and/or other image data.

Figure 18:
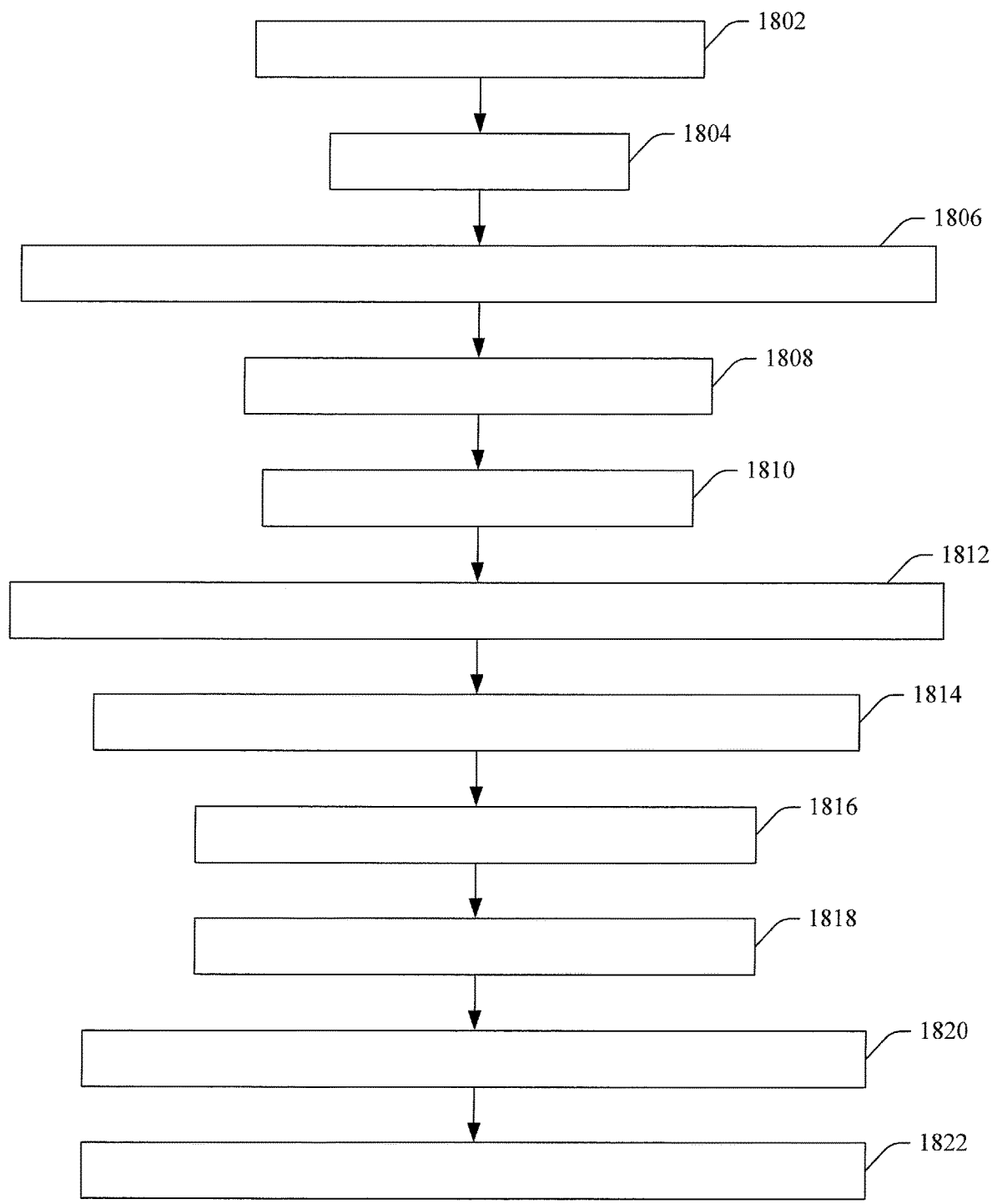
FIG. 18 illustrates an example method.

FIG. 18 illustrates a method for employing the probe 104.

It is to be appreciated that the order of the following acts is provided for explanatory purposes and is not limiting. As such, one or more of the following acts may occur in a different order. Furthermore, one or more of the following acts may be omitted and/or one or more additional acts may be added.

At 1802, the head 118 of the probe 204 is inserted into a cavity of a subject or object.

At 1804, the transducer array 126 of the probe 204 is excited to acquire image data of structure in the cavity.

At 1806, the image data is visually observed to locate a structure of interest in the cavity.

At 1808, the light source 140 of the probe 104 is activated, illuminating a region on the inside wall of the cavity.

At 1810, an operator presses on an outside surface of the cavity.

At 1812, a camera in the cavity acquires data showing the illuminated region and depressions from the pressing.

At 1814, an instrument insertion point is identified in response to a depression coinciding with the illuminated region.

At 1816, an instrument is inserted at the insertion point.

At 1818, the instrument is guided to the slot 402 of the instrument guide 142, under image data and/or other guidance.

At 1820, the instrument is advanced in the instrument guide 142 to the structure of interest, under guidance of the instrument guide and image data and/or other guidance.

At 1822, a procedure is performed on the structure of interest with the instrument.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound probe, comprising:
   an elongate shaft having a long axis, a first end, a second opposing end that spatially opposes the first end, a first side and a second opposing side that spatially opposes the first side;
   a probe head disposed at the first end and including:
      an ultrasonic window disposed on a sub-portion of only the first side; and
      a transducer array disposed behind the ultrasonic window and along the long axis, wherein the transducer array includes a transducing surface that is parallel to the long axis and transverse to the first and second ends and is configured to emit from the first side through the ultrasound window and in a first direction away from the probe head;
   a slot that extends entirely through the elongate shaft from the first side to the second opposing side, that is angled relative to the transducer array and the long axis of the elongate shaft, and that is configured as an instrument guide;
   a recess in a surface of the second side of the elongate shaft, spatially offset from the transducer array along the long axis, and angled relative to the transducer array and the long axis of the elongate shaft; and
   a light source disposed in the recess, angled relative to the transducer array and the long axis of the elongate shaft, and configured to emit light from the second side in a second direction away from the probe head, away from the first end, towards the second end, and opposite the first direction.

2. The ultrasound probe of claim 1, further comprising a second different window disposed in the recess between the light source and the second side of the elongate shaft.

3. The ultrasound probe of claim 1, wherein the transducer array, the light source, or both the transducer array and the light source are stationarily mounted in the probe.

4. The ultrasound probe of claim 1, wherein the slot has a diameter in a range of 0.413 millimeters to 3.00 millimeters.

5. The ultrasound probe of claim 1, wherein an instrument path of the slot and a light emission path of the recess are parallel to each other.

6. The ultrasound probe of claim 1, wherein the light source includes a laser, a light emitting diode, or an optical fiber.

7. The ultrasound probe of claim 1, wherein the slot is cylindrical in shape.

8. The ultrasound probe of claim 1, wherein an instrument path of the slot and a light emission path of the recess are not parallel to each other.

9. The method of claim 1, wherein the slot is located between the transducer array and the recess.

10. The ultrasound probe of claim 1, wherein the recess is located between the transducer array and the slot.

11. The ultrasound probe of claim 1, wherein an end of the light source is flush with the surface of the second side of the elongate shaft.

12. The ultrasound probe of claim 1, wherein the slot is inside of the recess and the light source includes only a single light emitting element that surrounds the outer perimeter of the slot.

13. The ultrasound probe of claim 1, wherein the light source is arranged with respect to the instrument guide to illuminate a region that aligns with a path traversing the slot.

14. The ultrasound probe of claim 1, wherein the light source is configured to produce light having a diameter in a range of one (1) millimeter to fifty (50) millimeters.

15. The ultrasound probe of claim 1, further comprising:
   a body with two ends; and
   a handle, wherein one of the two ends of the body is coupled to the probe head and the other of the two ends of the body is coupled to the handle.

16. The ultrasound probe of claim 15, the elongate shaft, further comprising:
   an articulating member that couples the probe head and the first end.

* * * * *